US010716950B2

(12) United States Patent
Best

(10) Patent No.: US 10,716,950 B2
(45) Date of Patent: *Jul. 21, 2020

(54) TREATMENT OF THALAMOCORTICAL DYSRHYTHMIA

(71) Applicant: Steven Richard Devore Best, Deerfield, IL (US)

(72) Inventor: Steven Richard Devore Best, Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/491,612

(22) Filed: Apr. 19, 2017

(65) Prior Publication Data

US 2018/0001104 A1    Jan. 4, 2018

Related U.S. Application Data

(63) Continuation of application No. 14/634,305, filed on Feb. 27, 2015, now Pat. No. 9,649,501, which is a continuation of application No. 13/826,250, filed on Mar. 14, 2013, now Pat. No. 8,974,365.

(60) Provisional application No. 61/729,625, filed on Nov. 25, 2012.

(51) Int. Cl.
| *A61N 2/00* | (2006.01) |
| *A61N 2/02* | (2006.01) |
| *A61M 19/00* | (2006.01) |
| *A61K 45/06* | (2006.01) |
| *A61K 31/135* | (2006.01) |
| *A61N 1/36* | (2006.01) |
| *A61M 15/00* | (2006.01) |
| *A61M 21/00* | (2006.01) |

(52) U.S. Cl.
CPC ............ *A61N 2/002* (2013.01); *A61K 31/135* (2013.01); *A61K 45/06* (2013.01); *A61M 15/00* (2013.01); *A61M 19/00* (2013.01); *A61N 1/36021* (2013.01); *A61N 1/36025* (2013.01); *A61N 2/006* (2013.01); *A61N 2/008* (2013.01); *A61N 2/02* (2013.01); *A61M 21/00* (2013.01); *A61M 2021/0055* (2013.01); *A61M 2202/048* (2013.01); *F04C 2270/0421* (2013.01)

(58) Field of Classification Search
CPC .......... A61N 2/00; A61N 2/002; A61N 2/004; A61N 2/006; A61N 2/008; A61N 2/02; A61N 2/12; A61N 1/36021; A61N 1/36025; A61N 1/36028
See application file for complete search history.

(56) References Cited

U.S. PATENT DOCUMENTS

| 5,084,007 A | 1/1992 | Malin et al. |
| 6,107,271 A | 8/2000 | Moskal et al. |
| 6,132,361 A | 10/2000 | Epstein et al. |
| 6,176,242 B1 | 1/2001 | Rise |
| 8,492,340 B2 | 7/2013 | Moskal |
| 8,674,095 B2 | 3/2014 | Campbell |
| 8,680,279 B2 | 3/2014 | Kamalesh Babu |
| 9,770,601 B2 | 9/2017 | Moses |
| 2006/0069086 A1 | 3/2006 | Michalow |
| 2006/0095088 A1 | 5/2006 | De Ridder |
| 2007/0287753 A1* | 12/2007 | Charney ............. A61K 9/0019 514/647 |
| 2008/0208287 A1* | 8/2008 | Palermo ............. A61N 1/0452 607/48 |
| 2010/0047342 A1 | 2/2010 | Went et al. |
| 2010/0184817 A1 | 7/2010 | Wolicki |
| 2011/0178441 A1 | 7/2011 | Tyler |
| 2011/0307029 A1 | 12/2011 | Hargrove |
| 2014/0058189 A1* | 2/2014 | Stubbeman ............ A61N 2/002 600/13 |

FOREIGN PATENT DOCUMENTS

WO    2011/123548    10/2011

OTHER PUBLICATIONS

Aan Het Rot et al., "Ketamine for Depression: Where do we go from Here?" Biol Psychiatry, 2012, pp. 537-547, vol. 72.

Akiskal et al., "The distinct temperament profiles of bipolar I, bipolar II and unipolar patients," Journal of Affective Disorders, 2006, pp. 19-33, vol. 92, No. 1.

Allan et al., "Transcranial Magnetic Stimulation in the Management of Mood Disorders," Neuropsychobiology, 2011, pp. 163-169, vol. 64.

Allen et al., "Transcranial magnetic stimulation elicits coupled neural and hemodynamic consequences," Science, 2007, pp. 1918-1921, vol. 317.

Allen et al., "The stability of resting frontal electroencephalographic asymmetry in depression," Psychophysiology, 2004, pp. 269-280, vol. 41.

Anderson et al., "Tolerability and safety of high daily doses of repetitive transcranial magnetic stimulation in healthy young men," J ECT, 2006, pp. 49-53, vol. 22.

Antal et al., "A case of refractory orofacial pain treated by transcranial direct current stimulation applied over hand motor area in combination with NMDA agonist drug intake," Brain Stimulation, 2011, pp. 117-121, vol. 4.

Asadabadi et al., "Celecoxib as adjunctive treatment to risperidone in children with autistic disorder: a randomized, double-blind, placebo-controlled trial," Psychopharmacology, 2012, pp. 51-59, vol. 225, No. 1.

(Continued)

*Primary Examiner* — Carrie R Dorna
(74) *Attorney, Agent, or Firm* — McDonnell Boehnen Hulbert & Berghoff LLP

(57) ABSTRACT

A method for treating conditions associated with thalamocortical dysrhythmia. The method includes applying transcranial low voltage electrical stimulation (TLVES) therapy or transcranial magnetic stimulation (TMS) therapy to a patient in need thereof, and administering to the patient a dissociative anesthetic during the TLVES therapy or the TMS therapy. A number of conditions including tinnitus, depression and pain can be treated with TLVES or TMS in combination with the dissociative anesthetic, such as an NMADR inhibitor, including ketamine.

40 Claims, No Drawings

(56) References Cited

OTHER PUBLICATIONS

Badaway et al., "The peri-ictal state: cortical excitablity changes within 24 h of a seizure," Brain, 2009, pp. 1013-1021, vol. 132.
Barker et al., "An introduction to the basic principles of magnetic nerve stimulation," J. Clin. Neurophysiol, 1991, pp. 26-37, vol. 8.
Been et al., "The Use of tDCS and CVS as Methods of Non-Invasive Brain Stimulation," Brain Research Reviews, 2007, pp. 346-361, vol. 56, No. 2.
Benes et al., "GABAergic Interneurons: Implications for Understanding Schizophrenia and Bipolar Disorder," Neuropsychopharmacology, 2001, pp. 1-27, vol. 25, No. 1.
Berman et al., "Antidepressant effects of ketamine in depressed patients," Biol. Psychiatry, 2000, pp. 351-354, vol. 47.
Bersani et al., "Deep transcranial magnetic stimulation as a treatment for psychiatric disorders: A comprehensive review," Eur Psychiatry, 2012, pp. 30-39, vol. 28.
Bloch et al., "Effects of ketamine in treatment-refractory obsessive-compulsive disorder," Biol Psychiatry, 2012, pp. 964-970, vol. 72, No. 11.
Bowirrat et al., "Neuro-psychopharmacogenetics and Neurological Antecedents of Posttraumatic Stress Disorder: Unlocking the Mysteries of Resilience and Vulnerability," Current Neuropharmacology, 2010, pp. 335-358, vol. 8.
Brainsway Reports Positive Pivotal Multicenter Major Depression Trial Results, 31 (Apr. 18, 2012).
Breier et al., "Association of ketamine-induced psychosis with focal activation of the prefrontal cortex in healthy volunteers," Am J Psychiatry, 1997, pp. 805-811, vol. 154.
Briggs et al., "Emerging views of corticothalamic function," Curr Opin Neurobiol., 2008, pp. 403-407, vol. 18.
Brown et al., "The Relationship of Personality to Mood and Anxiety States: a Dimensional Approach," J Psychiatr Res., 1992, pp. 197-211, vol. 26.
Buckner et al., "The brain's default network anatomy, function, and relevance to disease," Annals of the New York Academy of Sciences, 2008, pp. 1-38, vol. 1124.
Carpenter et al., "Transcranial magnetic stimulation (TMS) for major depression: A multisite, naturalistic, observational study of acute treatment outcomes in clinical practice," Depression and Anxiety, 2012, pp. 587-596, vol. 29.
Catafau, Anna M., "Brain SPECT in clinical practice. Part I: perfusion," J Nucl Med, 2001, pp. 259-271, vol. 42.
Cauda et al. "Low-Frequency BOLD Fluctuations Demonstrate Altered Thalamocortical Connectivity in Diabetic Neuropathic Pain," BMC Neuroscience, 2009, pp. 1-14, vol. 10, No. 138.
Cazzoli et al., "Theta burst stimulation reduces disability during the activities of daily living in spatial neglect," Brain, 2012, pp. 1-14.
Chan et al., "Augmenting Transcranial Direct Current Stimulation with D-cyloserine for Depression," Journal of ECT, 2013, pp. 196-200, vol. 29, No. 3.
Chang et al., "Reduction of dorsolateral prefrontal cortex gray matter in late-life depression," Psychiatry Res. Neuroimaging, 2011, pp. 1-6, vol. 193.
Chang et al., "Long-Term Effects of rTMS on Motor Recovery in Patients After Subacute Stroke," J. Rehabil Med., 2010, pp. 758-764, vol. 42.
Chio et al., "Therapeutic Evaluation of Etanercept in a Model of Traumatic Brain Injury," Journal of Neurochemistry, 2010, pp. 921-929, vol. 115.
Chen et al., "Maintenance therapy of celecoxib for major depression with mimicking neuropsychological dysfunction," General Hospital Psychiatry, 2010, pp. 1-3, vol. 32, No. 6.
Cohen et al., "Repetitive Transcranial Magnetic Stimulation of the Right Dorsolateral Prefrontal Cortex in Posttraumatic Stress Disorder: a Double-Blind, Placebo-Controlled Study," American Journal of Psychiatry, 2004, pp. 55-524, vol. 161, No. 3.
Corssen et al., "Changing concepts in pain control during surgery: Dissociative anesthesia with CI-581," Anesth Analg., 1968, pp. 746-759, vol. 47.
Crawford et al., "Hypnotic Analgesia: 1. Somatosensory Event-Related Potential Changes to Noxious Stimuli and 2. Transfer Learning to Reduce Chronic Low Back Pain," The International Journal of Clinical and Experimental Hypnosis, 1998, pp. 92-132, vol. 46, No. 1.
Crawford et al., "The Nature of Hypnotic Analgesia: Neurophysiological Foundation and Evidence," Contemporary Hypnosis, 1998, pp. 22-33, vol. 15.
Crawford, Helen J., "Brain Dynamics and Hypnosis: Attentional Disattentional Processes," The International Journal of Clinical and Experimental Hypnosis, 1994, pp. 204-232, vol. 42, No. 3.
Crown et al., "The impact of treatment-resistant depression on health care utilization and costs," J Clin Psych, 2002, pp. 963-971, vol. 63.
Cusin et al., "Somatic therapies for treatment-resistant depression: ECT, TMS, VNS, DBS," Biol Mood Anxiety Disord., 2012, 9 pages, vol. 2, No. 14.
Dale et al. "Infant Regulatory Disorders: Temperamental Physiological, and Behavioral Features," Journal of Developmental Behavioral Pediatrics, 2011, pp. 216-224, vol. 32.
Davis et al., "The brain's emotional foundations of human personality and the Affective Neuroscience Personality Scales," Neuroscience and Biobehavioral Reviews, 2011, pp. 1946-1958, vol. 35.
Deng et al., "Electric field depth-focality tradeoff in transcrancial magnetic stimulation: simulation comparison of 50 coil designs," Brain Stimul., 2013, pp. 1-13, vol. 6.
Di Lazzaro et al., "Ketamine increases human motor cortex excitability to transcranial magnetic stimulation," J. Physiol., 2003, pp. 485-496, vol. 547.
Diazgranados et al., "A randomized add-on trial of an n-methyl-d-aspartate antagonist in treatment-resistant bipolar depression," Arch Gen Psychiatry, 2010, pp. 793-802, vol. 67.
Diazgranados et al., "Rapid resolution of suicidal ideation after a single infusion of an N-methyl-D-aspartate antagonist in patients with treatment-resistant major depressive disorder," J. Clin. Psychiatry, 2010, pp. 1605-1611, vol. 71.
Dolberg et al. "Transcranial Magnetic Stimulation in Patients with Bipolar Depression: A Double-Blind, Controlled Study," Bipolar Disorders, 2002, pp. 94-95, vol. 4, No. 1.
Dubovsky, "Ketamine for Bipolar Depression," NEJM Journal Watch, Sep. 2012.
Dweck, Carol S., "Can Personality be Changed? The Role of Beliefs in Personality and Change," Current Directions in Psychological Science, 2008, pp. 391-394, vol. 17.
Eggermont et al., "The neuroscience of tinnitus," TRENDS in Neurosciences, 2004, pp. 676-682, vol. 27.
Egner et al., "Hypnosis decouples cognitive control from conflict monitoring processes of the frontal lobe," NeuroImage, 2005, pp. 969-978, vol. 27.
Eisenberger et al., "Why rejection hurts: a common neural alarm system for physical and social pain," Trends in Cognitive Sciences, 2004, pp. 294-300, vol. 8.
Esser et al., "Modeling the Effects of Transcranial Magnetic Stimulation on cCortical Circuits," J Neurophysiol., 2005, pp. 622-639, vol. 94.
Etkin et al., "Failure of Anterior Cingulate Activation and Connectivity with the Amygdala During implicit Regulation of Emotional Processing in Generalized Anxiety Disorder," American Journal of Psychiatry, 2010, pp. 545-554, vol. 167, No. 5.
Fava et al., "The problem of the placebo response in clinical trials for psychiatric disorders: Culprits, possible remedies, and a novel study design approach," Psychotherapy Psychosomatics, 2003, pp. 115-127, vol. 72.
Ferrarelli et al., "Reduced Evoked Gamma Oscillations in the Frontal Cortex in Schizophrenia Patients: A TMS/EEG Study," Am J Psychiatry, 2008, pp. 996-1005, vol. 165.
Fields, R. Douglas, "Amping Up Brain Function: Transcranial Stimulation Shows Promise in Speeding Up Learning," Scientific American, Nov. 25, 2011, vol. 25.
Fingelkurts et al., "Composition of brain oscillations in ongoing EEG during major depression disorder," Neurosci Res., 2006, pp. 133-144, No. 56.
Fox, Douglas., "Brain Buzz," Nature, 2011, pp. 156-158, vol. 472.

(56) References Cited

OTHER PUBLICATIONS

Fuggetta et al., "A neurophysiological insight into the potential link between transcranial magnetic stimulation, thalamocortical dysrhythmia and neuropsychiatric disorders," Experimental Neurology, 2012, pp. 1-9, vol. 245.
Gall et al., "Non-Invasive Electrical Brain Stimulation Induces Vision Restoration in Patients with Visual Pathway Damage," Graefes Arch Clin Exp Ophthalmol, Jun. 2012, pp. 1041-1043, vol. 251, No. 3.
Gersner et al., "Long-Term Effects of Repetitive Transcranial Magnetic Stimulation on Markers for Neuroplasticity: Differential Outcomes in Anesthetized and Awake Animals," Journal of Neuroscience, 2011, pp. 7521-7526, vol. 31.
Giles et al., "Controlled comparison of electrophysiological sleep in families of probands with unipolar depression," Am J Psychiatry, 1998, pp. 192-199, vol. 155.
GlobeNewsWire. "Brainsway Reports Positive Pivotal Multicenter Major Depression Trial Results," Apr. 2012.
Grisaru et al., "Transcranial Magnetic Stimulation in Mania: A Controlled Study," American Journal of Psychiatry, 1998, pp. 16-8-1610, vol. 155, No. 11.
Gross, et al., "Has repetitive transcranial magnetic stimulation (rTMS) treatment for depression improved? A systematic review and meta-analysis comparing the recent vs. the earlier rTMS studies," Acta Psychiatrica Scandinavica, 2007, pp. 165-173, vol. 116.
Guehl et al., "Tremor-related activity of neurons in the 'motor' thalamus: changes in firing rate and pattern in the MPTP vervet model of parkinsonism," Eur. J. Neurosci., 2003, pp. 2388-2400, vol. 17.
Hannestad et al., "Glucose Metabolism in the Insula and Cingulate is Affected by Systemic Inflammation in Humans," J. Nucl Med., 2012, pp. 601-607, vol. 53.
Hasan et al., "Direct-Current-Dependent Shift of Theta-Burst-Induced Plasticity in the Human Motor Cortex," Exp Brain Res, 2012, pp. 15-23, vol. 217.
Hayward et al., "Exploring the physiological effects of double-cone coil TMS over the medial frontal cortex on the anterior cingulate cortex: an H215O PET study," Eur J Neurosci, 2007, pp. 2224-2233, vol. 25, No. 7.
Hellmann et al., "Repetitive magnetic stimulation of human-derived neuron-like cells activates cAMP-CREB pathway," European Archives of Psychiatry and Clinical Neuroscience, 2012, pp. 87-91, vol. 262.
Hirschfeld et al., "Personality and depression. Empirical findings," Arch Gen Psychiatry, 1983, pp. 993-998, vol. 40.
Holman et al., "Functional brain SPECT: the emergence of a powerful clinical method," J Nucl Med, 1992, pp. 1888-1904, vol. 33.
Holtzheimer et al., "Accelerated Repetitive Transcranial Magnetic Stimulation for Treatment-Resistant Depression," Depress Anxiety, 2010, pp. 960-963, vol. 27.
Holtzheimer et al., "Neuromodulation for treatment-resistant depression," F1000 Medicine Reports, 2012, pp. 1-10, vol. 22.
Horton et al., "Increased anterior corpus callosum size associated positively with hypnotizability and the ability to control pain," Brain, 2004, pp. 1741-1747, vol. 127.
Hughes, John R., "Absence seizures: A review of recent reports with new concepts," Epilepsy and Behavior, 2009, pp. 404-412, vol. 15.
Ibrahim et al., "Course of improvement in depressive symptoms to a single intravenous infusion of ketamine vs add-on riluzole: Results from a 4-week, double-blind, placebo-controlled study," Neuropsychopharmacology, 2012, pp. 1526-1533, vol. 37.
Institute of Medicine of The National Academies of Science, Report Brief, Jun. 2011; (available at: http://www.iom.edu/~/media/Files/Report%20Files/2011/Relieving-Pain-in-America-A-Blueprint-for-Transforming-Prevention-Care-Education-Research/Pain%20Research%202011%20Report%20Brief.pdf.
Israel, J.A., "Remission in depression: Definition and initial treatment approaches," J Psychopharmacol., 2006 pp. 5-10, vol. 20.
Isserles et al., "Cognitive-emotional reactivation during deep transcranial magnetic stimulation over the prefrontal cortex of depressive patients affects antidepressant outcome," Journal of Affective Disorders, 2011, pp. 235-242, vol. 128.
Jarema et al., "Is the patient really the same after a major depressive episode?" Medicographia, 2009, pp. 164-174, vol. 31, No. 2.
Jeanmonod et al., "Neuropsychiatric thalamocortical dysrhythmia: surgical implications," Thalamus and Related Systems, 2003, pp. 103-113, vol. 2.
Jeanmonod et al., "The Human Thalamocortical Dysrhythmia: Pathophysiology and Treatment," Exceptional Conference, Sep. 23, 2011, IRCAD, Amphiteatre L. Hirsch, Hopital Civil, Strasbourg, France.
Jirsa et al., "Toward the Virtual Brain: Network Modeling of the Intact and the Damaged Brain," Achives Italiennes de Biologie, 2010, pp. 189-205, vol. 148.
Jobert et al., "Guidelines for the Recording and Evaluation of Pharmaco-EEG Data in Man: The International Pharmaco-EEG Society (IPEG)," Neuropsychobiology, 2012, pp. 201-220, vol. 66.
Johnson et al., "Using EEG to explore how rTMS produces its effects on behavior," Brain Topogr; 2010, pp. 281-293, vol. 22.
Juni et al., "Procedure guidelines for brain perfusion PSECT using 99mTc radiopharmaceuticals 3.0," J Nucl Med Technol, 2009, pp. 191-195, vol. 37.
Kanai et al., "Frequency-Dependent Electrical Stimulation of the Visual Cortex," Current Biology, 2008, pp. 1839-1843, vol. 18.
Kanda et al. "Transcranial Magnetic Stimulation (TMS) of the Sensorimotor Cortex and Medial Frontal Cortex Modifies Human Pain Perception," Clinical Neurophysiology, 2003, pp. 860-866, vol. 114.
Katalinic et al., "Ketamine as a new treatment for depression: A review of its efficacy and adverse effects," Am N Z J Psychiatry, 2013, pp. 691-692, vol. 47.
Kim et al., "Neural Spike Sorting Under Nearly 0-dB Signal-to-Noise Ratio Using Nonlinear Energy Operator and Artificial Neural-Network Classifier," IEEE Transactions on Biomedical Engineering, 2000, pp. 1406-1411, vol. 47, No. 10.
Klug et al., "Dysfunctional pain modulation in somatoform pain disorder patients," Eur Arch Psychiatry Clin Neurosci., 2011, pp. 267-275, vol. 261.
Kostopoulos, George K., "Involvement of the Thalamocortical System in Epileptic Loss of Consciousness," Epilepsia, 2001, pp. 13-19, vol. 42(Suppl. 3).
Kranaster et al., "Clinically favourable effects of ketamine as an anaesthetic for electroconvulsive therapy: a retrospective study," European Archives of Psychiatry and Clinical Neuroscience, 2011, pp. 575-582, vol. 261.
Kross et al., "Social rejection shares somatosensory representations with physical pain," PNAS, 2011, pp. 6270-6275, vol. 108.
Kupfer et al., "The application of EEG sleep for the differential diagnosis of affective disorders," Am J Psychiatry, 1978, pp. 69-74, vol. 135.
Kupfer et al., "EEG sleep changes as predictors in depression," Am J Psychiatry, 1976, pp. 622-626, vol. 133.
Kyle et al., "Novel glutamatergic drugs for the treatment of mood disorders," Neuropsych Disease and Treatment, 2013, pp. 1101-1112, vol. 9.
Lanius et al., "A review of neuro-imaging studies in PTSD: Heterogeneity of response to symptom provocation," J. Psychiatric Research, 2006, pp. 709-729, vol. 40.
Lanius et al., "Recall of emotional states in posttraumatic stress disorder: an fMRI investigation," Biol. Psychiatry, 2003, pp. 204-210, vol. 53.
Latremoliere et al. "Central Sensitization: A Generator of Pain Hypersensitivity by Central Neural Plasticity," The Journal of Pain, 2009, pp. 895-926, vol. 10, No. 9.
Raz et al., "Firing Patterns and correlations of Spontaneous Discharge of Pallidal Neurons in the Normal and the Tremulous 1-methyl-4-phenyl-1,2,3,6-tetrahydropyridine Vervet Model of Parkinsonism," J. Neurosci., 2000, pp. 8559-8571, vol. 20.

(56) References Cited

OTHER PUBLICATIONS

Riemann et al., "How to preserve the antidepressive effect of sleep deprivation: A comparison of sleep phase advance and sleep phase delay," Eur Arch Psychiatry Clin Neurosci., 1999, pp. 231-237, vol. 249.
Rosen et al., "Noninvasive Transcranial Brain Stimulation and Pain," Curr Pain Headache Rep., 2009, pp. 12-17, vol. 13, No. 1.
Rossi et al., "Prefrontal [correction of Prefontal] cortex in long-term memory: an "interference" approach using magnetic stimulation," Nature Neuroscience, 2001, pp. 948-952, vol. 4.
Rutherford et al., "A model of placebo response in antidepressant clinical trials," Am J Psychiatry, [Epub ahead of print] 1-11 (Jan. 15, 2013).
Rutherford et al., "Study Design Affects Participant Expectations—A Survey," J Clin Psychopharmacol., 2009, pp. 179-181, vol. 29.
Sackheim, Harrold A., "The definition and meaning of treatment-resistant depression," J Clin Psych, 2001, pp. 10-17, vol. 62.
Salvadore et al., "Increased anterior cingulate cortical activity in response to fearful faces: A neurophysiological biomarker that predicts rapid antidepressant response to ketamine," Biol Psychiatry, 2009, pp. 289-295, vol. 65.
Salvadore et al., "Anterior cingulate desynchronization and functional connectivity with the amygdala during a working memory task predict rapid antidepressant response to ketamine," Neuropsychopharmacology, 2010, pp. 1415-1422, vol. 35.
Santana et al., "Activation of thalamocortical networks by the N-methyl-D-aspartate receptor antagonist phencyclidine: Reversal by clozapine," Biol Psychiatry, 2011, pp. 918-927, vol. 69.
Sawaki et al., "A Common Neural Mechanism for Preventing and Terminating the Allocation of Attention," J. Neurosci., 2012, pp. 10725-10736, vol. 32.
Scheidegger et al., "Ketamine decreases resting state functional network connectivity in healthy subjects: Implications for antidepressant drug action," PLoS ONE, 2012, e44799, pp. 1-9, vol. 7, No. 9.
Schlaepfer et al., "WFSBP Guidelines on Brain Stimulation Treatments in Psychiatry," The World Journal of Biological Psychiatry, 2010, pp. 2-18, vol. 11.
Schnitzler et al., "Normal and pathological oscillatory communication in the brain," Nat Rev Neurosci., 2005, pp. 285-296, vol. 6.
Schulman et al., "Imaging of thalamocortical dysrhythmia in neuropsychiatry," Front Hum Neurosci, 2011, pp. 69, vol. 5.
Schulman et al., "Thalamocortical dysrhythmia syndrome: MEG imaging of neuropathic pain," Thalamus and Related Systems, 2005, pp. 33-39, vol. 3.
Sela et al., "Transcranial Alternating Current Stimulation Increases Risk-Taking Behavior in the Balloon Analog Risk Task," Frontiers in Neuroscience, Feb. 2012, vol. 6, No. 22.
Serrien et al., "Motor inhibition in patients with Gilles de la Tourette syndrome: functional activation patterns as revealed by EEG coherence," Brain, 2005, pp. 116-125, vol. 128.
Sheehan et al., "Review of two years of experiences with SPECT among psychiatric patients in a rural hospital setting," J Psychiatr Pract, 2008, pp. 318-323, vol. 14.
Sherman, S. Murray, "Thalamocortical Loops and Information Processing," Encyclopedia of Pain, 2007, pp. 2427-2431.
Sigtermans et al., "Ketamine produces effective and long-term pain relief in patients with Complex Regional Pain Syndrome Type 1," Pain, 2009, pp. 304-311, vol. 145.
Silberstein et al., "Patterning of globus pallidus local field potentials differs between Parkinson's disease and dystonia," Brain, 2003, pp. 259702608, vol. 126.
Simpson et al., "Cost-Effectiveness of Transcranial Magnetic Stimulation in the Treatment of Major Depression: a Health Economics Analysis," Advances in Therapy, 2009, pp. 346-368, vol. 26, No. 3.
Smith et al., "Antidepressant effects of sertraline associated with volume increases in dorsolateral prefrontal cortex," J Affect Disord, 2013, pp. 414-419, vol. 146.
Snyder et al., "Savant-like skills exposed in normal people by suppressing the left fronto-temporal lobe," J. Integrative Neurosci., 2003, pp. 149-158, vol. 2.
Spencer et al., "Abnormal Neural Synchrony in Schizophrenia," J. Neurosci., 2003, pp. 7407-7411, vol. 23.
Spencer et al., "Neural synchrony indexes disordered perception and cognition in schizophrenia," Proc. Natl Acad. Sci., 2004, pp. 17288-17293, vol. 101.
Stahl, Stephen M., "Psychiatry stress testing: Novel strategy for translational psychopharmacology (a commentary)," Neuropsychopharmacology, 2010, pp. 1413-1414, vol. 35.
Steriade et al., "Thalamocortical Oscillations in the Sleeping and Aroused Brain," Science, 1993, p. 679, vol. 262.
Sterman, et al., "Foundation and Practice of Neurofeedback for the Treatment of Epilepsy," Applied Psychophysiology and Biofeedback, 2006, pp. 1-17, vol. 31, No. 1.
Stern et al., "Persistent EEG Overactivation in the Cortical Pain Matrix of Neurogenic Pain Patients," Neuroimage, 2005, pp. 721-731, vol. 31, No. 2.
Takeuchi et al., "A Narcoleptic patient exhibiting hallucinations and delusion," Psychiatry and Clinical neurosciences, 2000, pp. 321-322, vol. 54.
Thut et al., "Rhythmic TMS Causes Local Entrainment of Natural Oscillatory Signatures," Current Biology, 2011, pp. 1176-1185, vol. 21.
Timmermann et al., "The cerebral oscillatory network of parkinsonian resting tremor," Brain, 2003, pp. 199-212, vol. 126(Pt 1).
Tobinick, Edward, "Perispinal etanercept: a new therapeutic paradigm in neurology," Expert Rev. Neurother., 2010, pp. 985-1002, vol. 10, No. 6.
Turi et al., "Functional Neuroimaging and Transcranial Electrical Stimulation," Clinical EEG and Neuroscience, Sep. 2010, pp. 200-208, vol. 43, No. 3.
Urbano et al., "Cocain Acute "Binge" Administration Results in Altered Thalamocortical Interactions in Mice," Biol Psychiatry, 2009, pp. 769-776, vol. 66.
Ursu et al., "Overactive action monitoring in obsessive-compulsive disorder Evidence from functional magnetic resonance imaging," Psychological Science, 2003, pp. 347-353, vol. 14, No. 4.
Van Gorp et al., "Adding Input Noise to Increase the Generalization of Neural Networks is a Bad Idea," Intelligent Engineering Systems Through Artificial Neural Networks, 1998, pp. 127-133, vol. 8.
Victor et al., "Mean-field modeling of thalamocortical dynamics and a model-driven approach to EEG analysis," PNAS, 2011, pp. 15631-15638, vol. 108.
Vitek, Jerrold L., "Pathophysiology of dystonia: a neuronal model," Movement Disorders, 2002, pp. S49-S62, vol. 17.
Vlodavsky et al. "Hyperbaris Oxygen Therapy Reduces Neuroinflammation and Expression of Matrix Metalloproteinase-9 in the Rat Model of Traumatic Brain Injury," Neuropathol Appl Neurobiol, 2006, pp. 40-50, vol. 32, No. 1.
Volkmann et al., "Central motor loop oscillations in parkinsonian resting tremor revealed by magnetoencephalography," Neurology, 1996, pp. 1359-1370, vol. 46, No. 5.
Walton et al., "Abnormal thalamocortical activity in patients with Complex Regional Pain Syndrome (CRPS) Type I," Pain, 2010, pp. 41-51, vol. 150.
Wang et al., "Repetitive transcranial magnetic stimulation enhances BDNF-TrkB signaling in both brain and lymphocyte," J Neurosci., 2011, pp. 11044-11054, vol. 31.
Warden et al., "STAR*D Project Results: A Comprehensive Review of Findings," Curr. Psychiatry Rep., 2007, pp. 449-459, vol. 9.
Whelan-Goodinson et al., "Predictors of Psychiatric Disorders Following Traumatic Brain Injury," J Head Trauma Rehabil., 2010, pp. 320-329, vol. 25, No. 5.
Wichmann et al., "The primate subthalamic nucleus. III. Changes in motor behavior and neuronal activity in the internal pallidum induced by subthalamic inactivation in the MPTP model of parkinsonism," J. Neurophysiol., 1994, pp. 521-530, vol. 72.
Wirz-Justice et al., "Chronotherapeutics (light and wake therapy) in affective disorders," Psychol Med., 2005, pp. 939-944, vol. 35.

(56) References Cited

OTHER PUBLICATIONS

Young, Simon N., "Biologic effects of mindfulness meditation: growing insights into neurobiologic aspects of the prevention of depression," J Psychiatry Neurosci., 2011, pp. 75-77, vol. 36, No. 2.

Young et al., "Disruption of the right temporoparietal junction with transcranial magnetic stimulation reduces the role of beliefs in moral judgments," Proc Natl Acad Sci., 2010, pp. 6753-6758, vol. 107.

Zaehle et al., "Transcranial Alternating Current Stimulation Enhances Individual Alpha Activity in Human EEG," PLoS ONE, e13766, 2010, pp. 1-7, vol. 5, No. 11.

Zarate et al., "Human Biomarkers of Rapid Antidepressant effects," Biol. Psychiatry, 2013, pp. 1142-1155, vol. 73.

Zarate et al., "A Randomized Trial of N-methyl-D-aspartate Antagonist in Treatment-Resistant Major Depression," Arch Gen Psychiatry, 2006, pp. 856-865, vol. 63.

Zarate et al., "Replication of ketamine's antidepressant efficacy in bipolar depression: A randomized controlled add-on trial," Biol. Psychiatry, 2012, pp. 939-946, vol. 71.

Zimmerman et al., "How Should Remission from Depression be Defined? The Depressed Patient's Perspective," Am J Psychiatry, 2006, pp. 148-150, vol. 163.

Leknes et al., "Relief as a Reward: Hedonic and Neural Responses to Safety from Pain," PLoS ONE, 2011, pp. 1-10, vol. 6.

Li et al. "Hyperbaric Oxygenation Therapy Alleviated Chronic Constrictive Injury-Induced Neuropathic Pain and Reduces Tumor Necrosis Factor-Alpha Production," Anesthesia and Analgesia, 2011, pp. 626-633, vol. 113.

Lisanby et al., "Daily left prefrontal repetitive transcranial magnetic stimulation in the acute treatment of major depression: Clinical predictors of outcome in a multisite, randomized controlled clinical trial," Neuropsychopharmacology, 2009, pp. 522-534, vol. 34.

Liu et al., "Studies of properties of "Pain Networks" as predictors of targets of stimulation for treatment of pain," Frontiers in Integrative Neuroscience, 2011, pp. 1-7, vol. 5.

Llinas et al., "Thalamocortical dysrhythmia: A neurological and neuropsychiatric syndrome characterized by magnetoencephalography," PNAS, 1999, pp. 15222-15227, vol. 96.

Llinas et al., "Rhythmic and Dysrhythmic Thalamocortical Dynamics: GABA Systems and the Edge Effect," TRENDS in Neurosciences, 2005, pp. 325-333, vol. 28, No. 6.

Loo et al., "Could Transcranial Direct Current Stimulation Have Unexpected Additional Benefits in the Treatment of Depression?" Expert Review of Neurotherapeutics, Aug. 2012, pp. 751-753, vol. 12, No. 7.

Loo et al., "Transcranial direct current stimulation for depression: 3-week, randomised, sham-controlled trial," The British Journal of Psychiatry, 2012, pp. 52-59, vol. 200.

Lou et al. "Self-Specific Processing in the Default Network: a Single-Pulse TMS Study," Exp Brain Res., 2010, pp. 27-38, vol. 207(1-2).

Luber et al., "Self-enhancement processing in the default network: a single-pulse TMS study," Exp Brain Res., 2012, pp. 177-187, vol. 223.

Malhorta et al., "Ketamine-induced exacerbation of psychotic symptoms and cognitive impairment in neuroleptic-free schizophrenics," Neuropsychopharmacol., 1997, pp. 141-150, vol. 17.

Mantovani et al., "Functional magnetic resonance imaging guided transcranial magnetic stimulation in obsessive-compulsive disorder," Biol Psychiatry, 2010, pp. e39-e40, vol. 67, No. 7.

Masellis et al., "Quality of life in OCD: differential impact of obsessions, compulsions, and depression comorbidity," Canadian J Psychiatry, 2003, pp. 72-77, vol. 48, No. 2.

Massimini et al., "Cortical mechanisms of loss of consciousness: Insight from TMS/EEG studies," Archives Italiennes de Biologie, 2012, pp. 44-55, vol. 150.

Mayberg, Helen S., "Modulating dysfunctional limbic-cortical circuits in depression: Towards development of brain-based algorithms for diagnosis and optimised treatment," BMJ, 2003, pp. 193-207, vol. 65.

Mayberg et al., "Deep brain stimulation for treatment-resistant depression," Neuron, 2005, pp. 651-660, vol. 45.

McAuley et al., "Physiological and pathological tremors and rhythmic central motor control," Brain, 2000, pp. 1545-1567, vol. 123.

McCormick, David A., "Are Thalamocortical Rhythms the Rosetta Stone of a Subset of Neurological Disorders?" Nature Medicine, 1999, pp. 1349-1351, vol. 5, No. 12.

McCormick, David A., "Cortical and Subcortical Generators of Normal and Abnormal Rhythmicity," International Review of Neurobiology, 2002, pp. 99-114, vol. 49.

McIntyre et al., "The Human Cost of Not Achieving Full Remission in Depression," Can J Psychiatry, 2004, pp. 10S-16S, vol. 49.

Milad et al., "Neurological basis of failure to recall extinction memory in posttraumatic stress disorder," Biol. Psychiatry, 2009, pp. 1075-1082, vol. 66.

Millan et al., "Cognitive dysfunction in psychiatric disorders: characteristics, causes and the quest for improved therapy," Nature Reviews, Drug Discovery, 2012, pp. 141-168, vol. 11.

Miller et al., "Cytokine Targets in the Brain: Impact on Neurotransmitters and neurocircuits," Depression and Anxiety, 2013, pp. 297-306, vol. 30, No. 4.

Milovanova et al. "Hyperbaric Oxygen Stimulates Vasculogenic Stem Cell Growth and Differentiation in Vivo," Journal of Applied Psysiology, 2009, pp. 711-728, vol. 106.

Minoshima et al., "Anatomical standardization: linear scaling and nonlinear warping of functional brain images," J. Nucl. Med, 1994, pp. 1528-1537, vol. 35.

Miyasaka et al., "Neuronal mechanisms of ketamine-induced anesthesia," Int J Neuropharmacol., 1968, pp. 557-573, vol. 7.

Moretti et al., "Comparison of Ketamine and Thiopental in Healthy Volunteers: Effects on Mental Status, Mood, and Personality," Anesthesia and Analgesia, 1984, pp. 1087-1096, vol. 63.

Muller et al., "Schizophrenia as an Inflammation-Mediated Dysbalance of Glutamatergic Neurotransmission," Neurotoxicity Research, 2006, pp. 131-148, vol. 10.

Muller et al., "Long-Term Repetitive Transcranial Magnetic Stimulation Increases the Expression of Brain-Derived Neurotrophic Factor and Cholecystokinin mRNA, but not Neuropeptide Tyrosine mRNA in Specific Areas of Rat Brain," Neuropsychopharmacology, 2000, pp. 205-215, vol. 23.

Muller, Norbert, "Inflammation and the glutamate system in schizophrenia: implications for therapeutic targets and drug development," Expert Opin. Ther. Targets, 2008, pp. 1497-1507, vol. 12, No. 12.

Murrough et al., "Rapid and longer-term antidepressant effects of repeated ketamine infusions in treatment resistant major depression," Biol Psychiatry [Epub ahead of print] (Jun. 26, 2012).

Murrough et al., "Antidepressant efficacy of ketamine in treatment-resistant major depression: a two-site randomized controlled trial," Am. J. Psychiatry, 2013, pp. 1134-1142, vol. 170.

Najjar et al., "Neuroinflammation and psychiatric illness," J Neuroinflam., 2013, pp. 1-24, vol. 10, No. 43.

National Institute of Mental Health, "The numbers count: Mental disorders in America," (available at: www.nimh.nih.gov/health/publications/the-numbers-count-mental-disorders-in-america/index.shtml) accessed on Apr. 3, 2013.

Nini et al., "Neurons in the globus pallidus do not show correlated activity in the normal monkey, but phase-locked oscillations appear in the MPTP model of parkinsonism," J. Neurophysiol., 1995, pp. 1800-1805, vol. 74.

Owen et al., "N-back working memory paradigm: A meta-analysis of normative functional neuroimaging studies," Human Brain Mapping, 2005, pp. 46-59, vol. 25, No. 1, doi:10 1002/hbm 20131.

O'Reardon et al., "Efficacy and safety of transcranial magnetic stimulation in the acute treatment of major depression: A multisite randomized controlled trial," Biol Psychiatry, 2007, pp. 1208-1216, vol. 62.

Pankevich et al., "Glutamate related biomarkers in drug development for disorders of the nervous system workshop summary," Institute of Medicine, of the National Academies, 2011.

Pascual-Leone et al., "Transcranial magnetic stimulation in cognitive neuroscience—virtual lesion, chronometry, and functional connectivity," Curr Opin Neurobiol, 2000, pp. 232-237, vol. 10.

(56) References Cited

OTHER PUBLICATIONS

Paulus, Walter, "Transcranial electrial stimulation (tES-tDCS; tRNS, tACS) methods," Neuropsychological Rehabilitation, 2011, pp. 602-617, vol. 21, No. 5.

Pavel et al. "Viewing the Functional Consequences of Traumatic Brain Injury by Using Brain SPECT," Brain and Cognition, 2006, pp. 211-213, vol. 60.

Pena-Gomez et al., "Down-Regulation of Negative Emotional Processing by Transcranial Direct Current Stimulation: Effects of Personality Characteristics," PLoS ONE, e22812, Jul. 2011, pp. 1-9, vol. 6, No. 7.

Pizzagalli, Diego A., "Frontocingulate dysfunction in depression: Toward biomarkers of treatment response," Neuropsychopharmacol Rev., 2011, pp. 183-206, vol. 36.

Plante et al., "Sleep disturbance in bipolar disorder: Therapeutic implications," Am J Psychiatry, 2008, pp. 830-843, vol. 165.

Pliszka et al. "Neuroimaging of inhibitory control areas in children with attention deficit hyperactivity disorder who were treatment naive or in long-term treatment," Am J Psychiatry, 2006, pp. 1052-1060, vol. 163.

Pollok et al., "The cerebral oscillatory network of volunatary tremor," J Physiol, 2003, pp. 871-878, vol. 554.

Preskorn, SH, "Ketamine: The Hopes and The Hurdles," Biol Psychiatry, 2012, pp. 522-523, vol. 72.

Proske et al., "A Computational Model of Thalamocortical Dysrhythmia," European Journal of Neuroscience, 2011, pp. 1281-1290, vol. 33.

Rakofsky et al., "Emerging targets for antidepressant therapies," Current Opinion in Chemical Biology, 2009, pp. 291-302, vol. 13.

Ambriz-Tututi et al., "Transcranial Magnetic Stimulation Reduces Nociceptive Threshold in Rats," Journal of Neuroscience Research, 2012, pp. 1085-1095, vol. 90.

Barr et al., "Repetitive transcranial magnetic stimulation and drug addiction," International Review of Psychiatry, 2011, pp. 454-466, vol. 23.

Chong et al., "Development of a Sublingual / Oral Formulation of Ketamine for Use in Neuropathic Pain," Clinical Drug Investigation, 2009, pp. 317-324, vol. 29.

Fuggetta and Noh. "A neurophysiological insight into the potential link between transcranial magnetic stimulation, thalamocortical dysrhythmia and neuropsychiatric disorders," Expermental Neurology, 2013, pp. 87-95, vol. 245.

Leung et al., "rTMS for Suppressing Neuropathic Pain: A Meta-Analysis," The Journal of Pain, 2009, pp. 1205-1216, vol. 10.

Marcondes et al., "Repetitive transcranial magnetic stimulation improve tinnitus in normal hearing patients: a double-blind controlled, clinical and neuroimaging outcome study," European Journal of Neurology, 2010, pp. 38-44, vol. 17.

Poon et al., "Evidence-based options for treatment-resistant adult bipolar disorder patients," Bipolar Disorders, 2012, pp. 573-584, vol. 14.

Suckfull et al., "A randomized, double-blind, placebo-controlled clinical trial to evaluate the efficacy and safety of neramexane in patients with moderate to severe subjective tinnitus," BMC Ear, Nose and Throat Disorders, 2011, pp. 1-10, vol. 11.

Matsumura et al., "Comparison Between Pharmacologic Evaluation and Repetitive Transcranial Magnetic Stimulation-Induced Analgesia in Poststroke Pain Patients," Neuromodulation, 2013, pp. 349-354, vol. 16.

* cited by examiner

TREATMENT OF THALAMOCORTICAL DYSRHYTHMIA

CROSS-REFERENCE TO RELATED APPLICATION

This application claims the benefit of U.S. Provisional Patent Application Ser. No. 61/729,625, filed Nov. 25, 2012, which is incorporated by reference in its entirety.

BACKGROUND

Neurological disorders strike millions of people worldwide. A number of these varied disorders are associated with thalamocortical dysrhythmia, which is generally identified by a set of neurological and psychiatric conditions produced by abnormal oscillatory activity in the major neural circuit that links the brain's thalamus and cortex. Different symptoms are produced depending on where in the brain the rhythm disruption is occurring, but the neuronal mechanisms are the same. The abnormal rhythmicity interferes with normal communication among and between different regions of the brain, and thereby impairs the motor and cognitive skills, and other neurological functions, that are controlled by those regions of the cortex. Among the disorders associated with thalamocortical dysrhythmia are neurogenic pain, Complex Regional Pain Syndrome (CRPS) also known as (RSD), obsessive-compulsive disorder, depression, panic disorder, Parkinson's disease, schizophrenia, rigidity, dystonia, tinnitus, tremor, epilepsy, and major mood disorders.

Many patients do not respond to traditional treatments for these disorders. For instance, STAR-D (Sequenced Treatment Alternatives to Relieve Depression) predicts that only a third of 20 million Americans diagnosed with a major mood disorder achieve full remission, with a significant patient population remaining refractory to pharmacologic interventions, even after attempts at treatment with trials of a variety of anti-depressant medicines. See The Numbers Count: Mental Disorders in America, National Institute of Mental Health (2012). Similarly, a third of the United States population suffers from chronic, non-remitting pain. At least 40% of the population experiences chronic pain when somatic and emotional sequelae are combined. See Institute of Medicine of The National Academies of Science, Report Brief, June 2011.

The application of novel brain stimulation techniques to treat depression, and possibly other neuropsychiatric disorders, is a new and rapidly growing field. These techniques, such as Transcranial Magnetic Stimulation (TMS) and Transcranial Low Voltage Electrical Stimulation (TLVES) (also known as Transcranial Electrical Stimulation (tES)), are emerging as promising approaches because of their relative ease of use, safety and neurobiological effects.

TLVES involves the use of weak electric currents (1-4 mAmps) passed through brain tissue via electrodes placed on the scalp. Effective electrode placement is known for conditions such as: acute pain, prophylaxis against migraine, for depression, and for auditory hallucinations. tES can be delivered in the form of tDCS (direct current stimulation), tACS (alternating current stimulation), or as tRNS (random noise stimulation), which is a purposefully chaotic current flow. With tES, many parameters can be altered including frequency and range of frequency, shape of wave, and offset (of mathematical base of oscillating wave). The stimulation can affect both background electrical state, or sometimes affect oscillatory state, or even alter neuronal firing. It induces lasting changes in neuronal excitability, as evidenced in physiological studies. This is presumably the mechanism by which repeated stimulation can lead to meaningful therapeutic effects, as seen in the clinic-based studies.

Depression has also been treated with Transcranial Magnetic Stimulation (TMS), which was first introduced in 1985 to demonstrate relatively painless activation of the neuronal systems. In recent years, TMS has been applied to investigate the integrity and consequence of an electromagnetic stimulus propogated along the corticoneuronal system. Most recently, commercial TMS systems have been developed to treat Major Depressive Disorder (MDD). For instance, the NEUROSTAR TMS THERAPY® System (Neuronetics, Inc.) is a 37-minute outpatient TMS procedure that is performed under the supervision of a psychiatrist. It does not require anaesthesia or sedation, and patients remain awake and alert during the procedure. The treatment is typically administered daily for about 4-6 weeks.

During NeuroStar TMS Therapy, magnetic field pulses are generated and aimed at the left, prefrontal cortex, which is an area of the brain that has been demonstrated to function abnormally in patients with depression. These TMS magnetic fields are similar in type and strength as those used in magnetic resonance imaging (MRI) machines. The magnetic field pulses pass unimpeded through the hair, skin, and skull and into the brain.

Once inside the brain, the magnetic field pulses are believed to induce an electrical change within the impacted neural network. The amount of electrical potential created is very small, and cannot be felt by the patient, but it can change the activity of the neural tissue and is thought to lead to the release of neurotransmitter chemicals such as serotonin, norepinephrine and dopamine. In addition, regional Cerebral Blood Flow (rCBF) can be directly altered by TMS.

One of the significant drawbacks of TMS is the need for several weeks of rigorously scheduled treatments which equates to a significant human burden in terms of time, money, and hassle, and which often results in poor patient compliance.

Aside from techniques such as TLVES and TMS, there are many pharmaceutical agents currently available for treating neurological disorders. These include, but are not limited to, anticonvulsants, antiepileptics, barbiturates, barbituric acid derivatives, anesthetic agents, tinnitus-treating agents, selective serotonin reuptake inhibitors, antidepressant agents, neuroleptic agents, antihypertensive agents, antipsychotic agents, calcium channel blockers, ACE inhibitors, and beta-blockers, mood stabilizers, and stimulants, and hallucinogens. However, many of such drugs are limited in their effectiveness and by their significant side effects. For example, many of these drugs are known to cause lightheadedness, depression, insomnia, weight change, sexual dysfunction, cognitive dysfunction, weakness, fatigue, hallucinations, and other side-effects that severely limit their use in the clinic.

Recently, there has been interest in the use of NMDA receptor antagonists for treating neuropsychiatric disorders. NDMA inhibitors are a class of psychopharmacologic agents that work to antagonize, or partially inhibit the action of, the N-methyl d-aspartate receptor (NMDAR). They are commonly used as anaesthesia in animals and humans. The state of anaesthesia they induce is referred to as dissociative anaesthesia. Several synthetic opioids also function as NMDAR-antagonists, such as Meperidine, Methadone, Dextropropoxyphene, Tramadol and Ketobemidone. Some NMDA receptor antagonists, including but not limited to ketamine, dextromethorphan, phencyclidine, and nitrous oxide are known for their dissociative, hallucinogenic, and/or euphoriant properties.

One particular NMDA inhibitor, ketamine, has been shown to be effective in treating depression in patients with bipolar disorder who have not responded to anti-depressants. See Preskorn, Biol. Psychiatry (2012) 72:522-23. In persons with major depressive disorder and bipolar depression, it can produce a rapid antidepressant effect, acting within two hours as opposed to the several weeks often needed by typical antidepressants to work. When used alone, ketamine appears to provide four to seven days of relief from suicidality. Ketamine does not, however, appear to provide lasting relief from suicidality or depression.

Accordingly, the inventors have identified a need for treatments of conditions associated with thalamocortical dysrhythmia that provide more robust and more consistent improvement. Such treatment should also provide a greater likelihood of lasting successful results. Still further, the treatment should preferably reduce the undesirable consequences of drug therapies.

The foregoing description in this section is not prior art to the claims in this application and is not admitted to be prior art by inclusion in this section.

SUMMARY

In one aspect, the disclosure is directed to a method for treating conditions associated with thalamocortical dysrhythmia in a patient. The method includes applying transcranial low voltage electrical stimulation (TLVES) therapy or transcranial magnetic stimulation (TMS) therapy to the patient, combined with administering to the patient a dissociative anesthetic during the TLVES therapy or the TMS therapy.

In various aspects of the disclosure, the condition associated with thalamocortical dysrhythmia may be tinnitus, pain, including Complex Regional Pain Syndrome or Reflex Sympathetic Dystrophy, and known forms of depression, including bipolar depression.

In another aspect, the dissociative anesthetic is an N-methyl d-aspartate receptor (NMDAR) antagonist, such as ketamine, which can be administered over the course of about 30 to 60 minutes. When the NMDAR antagonist is ketamine, the dose can be about 50-500 mg. Comparable therapeutic doses of other NMDAR antagonists may alternatively be used.

In yet another aspect, the TLVES therapy or TMS therapy is applied prior to, intermittently or consistently during, and after the administration of the NMDAR antagonist. In particular, the method may include a priming treatment applied prior to the application of TMS therapy combined with the dissociative anaesthetic.

Still further, another embodiment of the disclosure includes repeating the method of treatment at intervals of 3-7 days at least five times.

These as well as other aspects and advantages, and alternatives, will become apparent to those of ordinary skill in the art by reading the following detailed description, with reference where appropriate to the accompanying drawings.

DESCRIPTION

Exemplary systems and methods are described herein. It should be understood that the word "exemplary" is used herein to mean "serving as an example, instance, or illustration." Any embodiment or feature described herein as "exemplary" or an "example" is not necessarily to be construed as preferred or advantageous over other embodiments or features. The exemplary embodiments described herein are not meant to be limiting. It will be readily understood that certain aspects of the disclosed systems and methods can be arranged and combined in a wide variety of different configurations, all of which are contemplated herein.

In various aspects, the disclosure is directed to a method of treating a thalamocortical dysrhythmia disorder in a patient. The method includes administrating to the patient a therapeutically effective amount of a dissociative anesthetic in combination with transcranial electrical or electromagnetic stimulation, for example TMS, or transcranial low voltage electrical simulation (TLVES).

Non-limiting examples of the neurological disorder associated with thalamocortical dysrhythmia include: depression, chronic depression, bipolar depression, neurological pain or central pain, complex regional pain syndrome (CRPS) also known as reflex sympathetic dystrophy (RSD), obsessive-compulsive disorder, panic disorder, rigidity, dystonia, tinnitus, tremor, epilepsy, petitmal epilepsy; absence epilepsy, autism, Parkinson's disease; obsessive-compulsive disorder (OCD), schizophrenia, schizoaffective psychosis, migraine, and restless legs syndrome, among others. In addition, users of various substance of abuse, including such as heroin, opiates, cocaine, psychostimulants, alcohol and tranquilizers, are known to have thalamocortical dysrhythmia.

TMS involves creating and applying a fluctuating magnetic field in a controlled manner. The flux created by the expansion and contraction of the magnetic field creates electrical changes in the patient's tissue impacted by the TMS head coil. Sometimes the result is thought to depolarize neurons and to generate action potentials. Another possible result is thought to be alterations in electrical state of the cells affected by magnetic stimulation. One key advantage of TMS over TLVES is that TMS can be delivered to the brain in a more spatially focused way, particularly when a figure-of-eight coil is used. One parameter in TMS treatment as described herein is the electromagnetic frequency used to effect stimulation of the brain tissue. For example, stimulation frequencies at 1 Hz or below may be used in connection with the TMS treatment described herein. TMS treatments at 1 Hz or below have also been called single-pulse TMS, although this term is generally used to describe TMS delivered every few seconds at random intervals. TMS delivered at higher frequency may also be used in connection with the TMS treatment described herein, although such TMS treatment at higher frequency is sometimes described as repetitive TMS (rTMS). The inhibitory and excitatory effects of TMS have been postulated to be akin to long-term potentiation and long-term depression. Another approach is to deliver bursts of stimulation repeatedly, as is the case with theta-burst stimulation (TBS), so that the initial stimulation primes the system for the later stimulation.

Transcranial electrical stimulation administered in low voltages (generally less than about 20 volts) takes several forms, including fixed current DC stimulation (tDCS), alternating current stimulation (tACS), or random (noise) current generation (tRNS). The dose associated with the transcranial low voltage electrical stimulation (TLVES) can be defined with regard to the size and position of the electrodes on the skull and the duration, frequency and intensity (in mAmps) of current. A current of less than about 4 mAmps is commonly used in these techniques. In some embodiments, a commercially available computer controlled DC stimulator may be used.

Although the transcranial electrical and electromagnetic stimulation parameters described herein can be consistent across a relatively broad range of individuals, it should be recognized that there are differences in individual responsiveness to electrical or electromagnetic stimulation for any given individual. One way in which the intensity of the stimulation has typically been calibrated for a given individual is testing the person to derive the minimal intensity of stimulation applied to the motor cortex (often referred to as M1) that evokes a motor response. This motor threshold is generally reported as the minimum intensity required to effectuate stimulation, and may be defined in terms of a percentage of the device's available output or may alternatively be defined in terms of the strength of field measures, i.e., Tesla units. In any event, the degree to which stimulation effects the treatment of a particular patient may be influenced by the stimulation frequency, the treatment repetition frequency (including any pretreatment as described below), and the personal response characteristics of the particular patient. These and similar individual variabilities in response seem to attributable to individual physiology and chemistry, which may be genetically determined at least in part. Specific TMS parameters include the inter-train interval (time between trains of stimulation), number of trains per session, and duration of the session. The most common discomforts are headaches, scalp pain, nausea, and transient hearing difficulty (participants wear ear plugs to avoid this), and these factors too may affect the manner in which patients respond to the treatment. Thus, it should be understood that practicing the methods of described herein on any patient will require the practitioner to exercise a certain amount of experience and judgment to accommodate the patient's individual sensitivities. For example, when a clinician may recognize in advance that a certain patient appears to be medically or psychologically frail in ways that suggest the patient is not a good candidate for TMS, or when a patient may want to avoid TMS therapy, tES treatment offers an effective alternative approach. tES treatment offers an important clinical benefit for patients who may not be good candidates for TMS treatment. Additionally, tES can be important as an effective transition therapy for patients who are sensitive to the adverse effects of TMS treatment.

NMDA receptor antagonists are a class of dissociative anaesthetics that work to antagonize, or inhibit the action of, the N-methyl d-aspartate receptor (NMDAR). They are used as anesthesia for animals and, less commonly, for humans. The state of anesthesia they induce is referred to as dissociative anesthesia. The NMDA receptor is an ionotropic receptor that allows for the transfer of electrical signals between neurons in the brain and in the spinal column. For electrical signals to pass, the NMDA receptor must be open. To remain open, glutamate and glycine must bind to the NMDA receptor. An NMDA receptor that has glycine and glutamate bound to it and has an open ion channel is called "activated."

Ketamine, ((RS)-2-(2-Chlorophenyl)-2-(methylamino) cyclohexanone), is a drug used in human and veterinary medicine. Ketamine is primarily used for the induction and maintenance of general anesthesia, usually in combination with a sedative. Other uses include sedation in intensive care, analgesia (particularly in emergency medicine), and treatment of bronchospasm. Ketamine has a wide range of effects in humans, including analgesia, anesthesia, hallucinations, elevated blood pressure, and bronchodilation, and it maintains perfusion of the brain and heart tissue.

Ketamine has been shown to be effective in treating depression in patients with bipolar disorder who have not responded to anti-depressants. In particular, it is known to cause relief from suicidality. In persons with major depressive disorder, it produces a rapid antidepressant effect, acting within two hours as opposed to the several weeks taken by typical antidepressants to work.

Ketamine has also being used as an experimental and controversial treatment for Complex Regional Pain Syndrome (CRPS) also known as Reflex Sympathetic Dystrophy (RSD). CRPS/RSD is a severe chronic pain condition characterized by sensory, autonomic, motor and dystrophic signs and symptoms. The pain in CRPS is continuous, it often worsens over time, and it is usually disproportionate to the severity and duration of the inciting event. In obsessive-compulsive disorder (OCD) patients infused with ketamine, the benefit is rather more limited than the above illnesses. (Pittenger, et al., Biol Psychiatry (2012) 72:964-970.)

Other NMDA receptor antagonists include Adamantanes, Amantadine, Memantine, Rimantadine, Arylcyclohexylamines, Dieticyclidine, Esketamine, Eticyclidine, Gacyclidine, Metaphit, Methoxetamine, Neramexane, Phencyclidine, Phenylhexylcyclopyrrolidine, Rolicyclidine, Tenocyclidine, Tiletamine, Methoxydine (4-MeO-PCP), Morphinans, Dextromethorphan, Dextrorphan, Methorphan, Morphanol, 2-MDP, 8A-PDHQ, Aptiganel, Dexoxadrol, Diethyl ether, Dizocilpine, Etoxadrol, Ibogaine (found in Tabernanthe iboga), Midafotel, NEFA, Nitrous oxide, Noribogaine, Perzinfotel, Remacemide, Selfotel, and Xenon.

In one aspect, the disclosure is directed to a method for treating a condition associated with thalamocortical dysrhythmia. The method includes treating a patient with transcranial electrical or electromagnetic stimulation, for example TMS or TLVES, in combination with a dissociative anesthetic. In one aspect, the dissociative anesthetic is an NMDAR inhibitor, for example, ketamine. Use of electrical or electromagnetic stimulation in combination with the dissociative anesthetic such as ketamine results in an improved therapeutic response, often at a reduced dosage of the dissociative anesthetic, as compared to the dosage that is typically necessary for treatment in the absence of the stimulation. For example, when used in combination with TMS, the dosage for ketamine can be from about 10 mg to about 500 mg delivered in a standard commercial formulation over the course of the TMS treatment. More particularly, the ketamine dose can range from about 20 mg to about 400 mg, particularly about 50 mg to about 350 mg, more particularly about 100 mg to 350 mg, and even more particularly about 200 mg to about 300 mg.

The combination treatment (i.e. stimulation in combination with the anesthetic) can extend from approximately 20 minutes to about 120 minutes at an appropriate dosage level. In particular, the period of stimulation can extend from approximately 20 minutes to about 100 minutes, from about 30 minutes to about 90 minutes, from about 40 minutes to about 100 minutes, or more particularly about 20, 30, 40, 50, 60, 70 80, 90, 110, or 120 minutes. In one specific example, a ketamine dose between about 50 and 350 mg is infused within the course of a TMS treatment extending approximately 20-60 minutes. In addition, longer infusion times can provide for a more gentle delivery of ketamine to the patient, and generally result in a better mood and less side effects.

During the combination treatment, the electrical or electromagnetic stimulation occurs during, and optionally before and/or after, the administration of the anesthetic. For example, the administration of the anesthetic can be preceded by a period of stimulation of approximately 1 to 15 minutes, more particularly approximately 3 to 10 min, or even more particularly in the range of about 5 min. Following this preceding period of stimulation, the administration of the anesthetic can begin, and the stimulation can then continue during the course of the administration. Following the administration of the anesthetic, the stimulation can be continued thereafter for approximately 1 to 15 minutes, more particularly approximately 3 to 10 min, or even more particularly in the range of about 5 min.

During a combination treatment using TMS, the TMS head-coil is directed towards the anterior cingulate region for treatment of a majority of the disorders associated with thalamocortical dysrhythmia. When treating tinnitus, stimulation of the association cortex may be appropriate. As more is learned in the future about which regions of the brain are involved in additional various health conditions, it may become more clear as to which regions of the brain should be the focus of stimulation for treatment of such additional health conditions.

The appropriate dose for the TMS treatment may be approximately 80% to 120% of a patient's motor threshold. As understood by one of skilled in the art, a patient's motor threshold reflects the amount of TMS power output at which a patient's thumb will begin to twitch when the TMS is directed to the relevant region of motor strip. It is relevant to brain stimulation as providing one simple way to operate within established safety parameters. More particularly, the appropriate dose for TMS treatment is approximately 90% to 120%, 100% to 120%, or 105% to 115% of a patient's motor threshold. One particular example, the appropriate dose for the TMS treatment is 110% of a patient's motor threshold. Generally, the frequency of the dose is 1 Hz and stimulation is continuous during the combination treatment described herein.

Similar methods are known to those of skill in the art for establishing the appropriate degree and location of stimulation for TLVES. For example, with TLVES, placement of the electrodes can be anterior-posterior (e.g., at mid-forehead and at the center of the back of the head or Oz). Usually, the patient can be treated for 10-50 minutes at 1,000 to 2,500 pAmps, for example about 15, 25, 25 or 45 minutes at about 1,000, 1,200, 1,300, 1,500, 2,000 or 2,500 pAmps. The stimulation may include an offset of about 800 to about 1200 pAmps, for example about 1000 pAmps. TLVES may be continuous during the combination treatment as described herein. In addition, the TLVES may be started before the infusion of a dissociative anesthetic, for example about 1-15 minutes before the start of the infusion, more particularly, for example, about 1, 2, 5, 10 or 15 minutes before the start of the infusion. The TLVES can also continue for a finite time once the infusion is complete.

The dissociative anesthetic can be delivered to the patient by any traditional delivery method, including intravenously, intramuscularly, orally, intranasally, and, when appropriate, by inhalation. Depending on the anesthetic, its half-life, delivery method and absorption rate, the time of the stimulation during the combination treatment can be adjusted to ensure that the anesthetic is present in therapeutically effective amounts during the stimulation. When the anesthetic is delivered intravenously, the patient experiences its effects essentially immediately. If the anesthetic is delivered orally, additional time can be added to the stimulation to ensure that the stimulation occurs while the anesthetic is therapeutically effective. The pharmacokinetics of ketamine and other dissociative anesthetics are relatively well studied by others in the art, and the understanding derived from those studies provides an adequate basis for predicting the relationship between the time, method, and amount of drug dosing in order to target the time for the anesthetic to enter the bloodstream and become available for treatment to the patient's tissue.

Prior to the combination treatment, the patient may undergo a priming stimulation treatment of approximately 10 to 80 minutes. For example, when TMS is used in the combination treatment, the TMS head-coil is directed at the left and right dorsilateral prefrontal cortices during the priming treatment for approximately 10 to 40 minutes each. The frequency for the priming TMS treatment can be about 1 Hz for the right prefrontal cortex and about 1 Hz for the left prefrontal cortex. The combination treatment can follow immediately after the completion of the priming TMS treatment, or the combination treatment can follow up to one day after the priming treatment, depending on patient tolerance and compliance. Priming with other forms of electrical or electromagnetic stimulation can also be used depending on patient need and tolerance.

In yet another alternative, a patient may be pretreated with electrical or electromagnetic stimulation for weeks or days prior to the combination treatment. For patients that are pretreated, the priming is not necessary. Accordingly, after a series of pretreatments, the combination treatment can begin, for example, the following day. When the combination treatment uses TMS, the pretreatment usually involves from about three days to two weeks of daily (approximately six out of seven days) TMS treatment using a therapeutic regimen. For example, the pretreatment may involve up to four TMS treatment sessions per day for one-half hour with 45 minutes between treatment sessions. As one example, the pretreatment sessions include stimulation at one Hz directed at the dorsilateral prefrontal cortex (left), stimulation at 10 Hz directed again to the left prefrontal cortex, stimulation at 20 Hz to the right prefrontal cortex, and stimulation at 20 Hz to the region overlaying the anterior cingulate region.

Some patients are apprehensive about treatment with ketamine and may be susceptible to fear. Accordingly, use of anti-anxiety medications such as Valium (diazepam) or Versed (midazolam) are appropriate. In addition, anti-nausea medications, such as Zofran (Ondansetron), may be appropriate for some patients.

Significant positive outcomes have been associated with the combination of TMS treatment plus ketamine when the combination is delivered on a weekly or bi-weekly basis. Other alternatives include, for example, treatment every 2, 3, 4, 5, 6, 8, 9, 10, 11, 12, 13, 15, 16, 17 18, 19, 20, 21 days or more. In some instances, patients abandon therapy for a variety of reasons, but resume after a number of weeks or even months. Positive outcome can be expected after about 2-20, more particular about 5-15 treatments, at regular intervals of about 3-11 days, more particularly about weekly. In addition, positive outcomes have been achieved with longer or shorter intervals, which may be sporadic due to patient scheduling and compliance issues. In particular examples, depression can be successfully treated with at least about 5 treatment sessions, more particularly about 6-8 treatments session, while chronic pain may take several additional treatment sessions to achieve the desired outcome, especially when the pain is accompanied by severe depression and/or addiction. In some instances, a patient may be given ongoing infrequent treatments (e.g., every one to four months) for maintenance purposes.

The use of TMS alone is reported effective in about 20-30% of patients for the treatment of mild to moderate depressions. TMS is reportedly even less effective in treating severe depression. Studies have suggested that the use of ketamine alone in the treatment of depression results in about a 60-70% success rate. However, in order to achieve this success for ketamine alone, the dosages for ketamine are reportedly 5-15 times higher than the dose necessary when ketamine is used in combination with TMS as described herein. In addition, relief with ketamine alone appears to be highly transitory in the ketamine-alone studies.

In comparison, the percentage of patients that completed treatment with a combination of TMS plus ketamine achieved a positive outcome is higher that the success rate reported with either TMS alone or ketamine alone. Moreover, the patients having positive outcomes from treatment with the combination of TMS plus ketamine, as described herein, tended to achieve a more robust, i.e., long lasting, positive result, and did so with reduced adverse side effects. Positive outcomes include return to work, rehabilitating a failing business, return to college, marriage, reconciling a failing relationship, dependable sobriety from substance abuse, and dramatic reductions in destructive doses of opioid narcotics. Moreover, many patients who achieved positive results after receiving the combination therapy described herein had previously failed all other treatments for their conditions. Those treatments included rTMS, VNS, TLVES, ECT, hyperbaric oxygen treatments, medications including ketamine (alone) infusions, and alternative medicine treatments like homeopathy.

Accordingly, the treatment described provides for better outcomes using less anesthetic in combination with TMS or TLVES. Because less anesthetic is necessary, the treatment results in fewer side effects. In addition, the need for less TMS or TLVES results in better patient compliance, which itself contributes to more positive outcomes. Indeed, patients who initially experience relief from the treatment tend to be motivated to receive additional treatments that provide a lasting benefit.

TLVES/ketamine treatment offers clinical benefit for patients who may not be good candidates for TMS/ketamine treatment. In particular, a clinician may recognize in advance that a certain patient is not a good candidate for TMS. For example, a patient may get more benefit by TLVES/ketamine because the patient becomes too fatigued by the potent effect of TMS/ketamine on overall CBF (cerebral blood flow). Or a patient may become agitated and require extraordinary nursing care to stay in position for the lengthy TMS/ketamine session. TLVES/ketamine treatment offers an effective alternative approach. In addition, TLVES/ketamine can be important as an effective transition therapy for patients who are sensitive to the adverse effects of TMS/ketamine treatment. TLVES/ketamine can be less taxing for the less robust people, and thus a good choice for those people once they are already on the path to stable recovery.

In another aspect, the disclosure is directed to a method of preventing side effects associated with the treatment of conditions associated with thalamocortical dysrhythmia with dissociative anesthetics. For example, the side effects can be minimized or prevented by using less anesthetic to treat patients. In this method, the dissociative anesthetic is administered in combination with TMS or TLVES. Similarly, in another aspect, the disclosure is directed to a method of reducing the dose of a dissociative anesthetic for treating a condition associated with thalamocortical dysrhythmia. In these aspects, the dose of the anesthetic can be reduced by about 2-20 times the amount normally administered for treatment of the conditions. In other aspects, the dose can be reduced 5-15 times, more particularly 10-15 times, and even more particularly, about 5, 10 or 15 times. In a particular example where the dissociative anesthetic is ketamine, the dose for treating the condition is from about 20 mg to about 400 mg, about 50 mg to about 350 mg, more particularly about 100 mg to 350 mg, and even more particularly about 200 mg to about 300 mg. In another example where the dissociative anesthetic is ketamine, the dose for treating the condition is from about 0.1-6.0 mg/kg, more particularly about 0.5-5.0 mg/kg, even more particularly, about 1.0-4.0 mg/kg.

EXAMPLES

Example 1: TMS/Ketamine Treatment

Thirty-five patients were treated with a combination of ketamine and TMS. All of the 28 patients that completed treatment identified in Table 1 had a positive outcome with the treatment regimen identified in Table 2 (Tables 1 and 2 appear at the end of specification prior to the claims). For simplicity of presentation in Table 2, patients receiving treatment more than once a week are shown as receiving a single treatment for that week. Also, intervals are rounded to the nearest week.

Some patients received a pretreatment (PT) for 3 days to two weeks of daily (usually 6 or 7 days) TMS treatment (generally indicated on FIG. 2 as "PT days" or "PT weeks"). Others received a priming TMS treatment prior to the combination treatment. Some patients received neither pretreatment nor priming, although most patients received one or the other. Since the priming treatment is less rigorous than several days of pretreatment, all patients receiving pretreatment were ultimately switched to priming or neither. Pretreatment and or priming treatment were administered based upon diagnosis and patient compliance. Patients suffering from chronic pain generally responded better when pretreatment or priming was administered, while the difference in depressed patients was less pronounced.

Based upon lack of success reported in previous studies with the use of ketamine alone, TMS alone, or TLVES alone, the positive outcomes shown in Table 1 suggest the synergistic effect of a combination therapy with ketamine and TMS. Moreover, patients receiving the combination therapy appear to have a lasting result which has not previously been reported with ketamine alone and is achieved at significantly lower doses of ketamine than previously understood.

Example 2: TLVES/Ketamine Treatment

Three patients were previously treated with TMS/ketamine as described above and had significantly improved. However, these patients were more frail and less robust than the other members of the cohort.

The patients were treated with either tACS or tRNS by defining the anode at F3 and the cathode at F8 in relation to net current flow. Electrical stimulation of the electrodes was applied for 20 minutes. Ketamine was started after 5 minutes and infused continuously for 15-50 minutes for a total dose of 0.5-5.0 mg per kg. For tACS, the parameters were 1200 µAmps, no offset or 1200 µAmps with 1000 µAmp offset. For tRNS, the parameters were 1300 or 2000 µAmps with 1000 µAmp offset. With TLVES/ketamine, all three patients have been able to get the same therapeutic benefits as TMS/ketamine with less of the post-treatment fatigue.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

TABLE 1

| ID | Diagnosis | Outcome | Overall Response |
|---|---|---|---|
| B23 | Fibromyalgia, PTSD, mixed connective tissue disease | off pain medicine, calm, more active, experienced severe nausea | excellent |
| B26 | Bipolar Disorder, poly-substance abuse | returned to college, got married | excellent |
| B3 | Unipolar Depression & ADD | entered graduate school, got out of abusive relationship | excellent |
| B6 | Bipolar Depression | entered graduate school, began to date for first time | excellent |
| C11 | Tourette's and secondary depression | off of inappropriate medicines, calm, in school | good |
| D20 | Depression & frontal lobe disorder | depression lifted, apathy lifted, pace of thought improved | excellent |
| D8 | OCD & secondary depression | back to work and active family life | good |
| H2 | Bipolar Depression | returned to home-life and active mothering | good |
| K10 | CRPS & regulatory disorder of childhood | off of opioid narcotics, entered trade school, saved subject's life | excellent |
| M12 | Unipolar Depression & minor epilepsy | did very well, went back to work, then stopped treatment and relapsed | good |
| M19 | Depression & poly-substance abuse | sober, active with family business | excellent |
| M25 | Panic disorder, secondary depression, dormant alcohol abuse | entered graduate school, sober, back to church life | excellent |
| M33 | Bipolar Disorder, poly-substance abuse | calm, still in early stage of treatment | very good |
| N13 | Bipolar Disorder & chronic neck and back pain | off of all opioid narcotics, calm, walking well | very good |
| N14 | Unipolar Depression, ADD, alcohol abuse, concussion | calm, repaired broken business & family life, sober | very good |
| N30 | Depression, fibromyalgia, back pain | off opioid narcotics, not depressed, traveling | excellent |
| N7 | Multiple head injuries and depression | off of all opioid narcotics, back to church life | excellent |
| O34 | ADHD, concussion, back pain, substance abuse | did very well, significant other coaxed subject back to substance abuse | excellent |
| Q9 | Bipolar Depression | back to work, repaired broken marriage | excellent |
| R17 | Childhood depression, PTSD, poly-substance abuse | learned to read, entered college, sober | excellent |
| R32 | OCD & secondary depression, poly-substance abuse | sober, calm, back to college | excellent |
| S1 | Generalized anxiety & secondary depression | returned to college, sober | excellent |
| S36 | Depression, panic attacks | did very well, repaired broken marriage and family | excellent |
| T15 | Bipolar Depression | back to church life and active family life | excellent |
| T29 | Bipolar Disorder, dormant poly-substance abuse | entered graduate school, running family business, still sober | excellent |
| W24 | Depression | back to work and active family life | excellent |
| Z27 | Childhood onset bipolar disorder, ADD, RSD | sober, calm, entered college and at work part-time | very good |
| Z4 | Unipolar Depression & ADD | no longer bedridden, left bad marriage | very good |

TABLE 2

| Week | B23 | B26 | B3 | B6 | C11 | D20 | D8 | H2 | K10 | M12 | M19 | M25 | M33 | N13 | N14 | N30 | N7 | O34 | Q9 | R17 | R32 | S1 | S36 | T15 | T29 | W24 | Z27 | Z34 |
|---|---|---|---|---|---|---|---|---|---|---|---|---|---|---|---|---|---|---|---|---|---|---|---|---|---|---|---|---|
| ID PT days | Y | Y | Y | Y | N | N | Y | Y | Y | Y | Y | Y | N | N | Y | N | N | Y | Y | N | N | Y | Y | Y | Y | N | Y | Y |
| PT weeks | Y | Y | Y | Y | N | N | Y | Y | N | Y | Y | Y | N | N | Y | N | N | Y | Y | N | N | Y | Y | Y | Y | N | Y | Y |
| Dose (mg, Ketamine) | | | | | | | | | | | | | | | | | | | | | | | | | | | | |
| 1 | 20 | 25 | 30 | 33 | | | 25 | 25 | 25 | 28 | | 60 | 50 | 25 | 45 | 35 | 25 | 25 | 65 | 25 | 25 | 25 | 25 | 25 | 25 | | 30 | 35 |
| 2 | 30 | 35 | 30 | 33 | | | 30 | 35 | | 30 | | | 50 | 50 | 40 | 40 | 50 | 40 | | 50 | 50 | 35 | | 40 | 35 | | 30 | |
| 3 | 40 | 40 | 40 | 33 | 25 | 25 | 45 | 45 | | 30 | | 60 | 75 | 70 | 40 | 45 | 45 | 50 | | 75 | 75 | 45 | 30 | | 50 | 50 | 38 | |
| 4 | 50 | | 50 | 33 | 50 | | 55 | 60 | 50 | 60 | 45 | | 100 | 110 | 40 | 50 | 45 | | | 100 | 100 | | 40 | | 60 | 75 | 40 | 35 |
| 5 | 55 | | 55 | 33 | 75 | 50 | 70 | 55 | 74 | 75 | | | 125 | 125 | | 75 | 42 | 50 | | 115 | 125 | | | | | 100 | | |
| 6 | 60 | 60 | 60 | 33 | 100 | 65 | 85 | 65 | 100 | 75 | 45 | 60 | 125 | 175 | 35 | 60 | 40 | | | 130 | 150 | | 40 | 40 | 45 | 120 | 55 | |
| 7 | 65 | 75 | 60 | 30 | 150 | 65 | | 75 | 125 | 75 | 45 | 60 | | 200 | 35 | 55 | 40 | | | 145 | | | | 50 | | 145 | 55 | |
| 8 | 70 | | 70 | 33 | 200 | 75 | 80 | 85 | 150 | 105 | 45 | 60 | | 225 | 35 | 60 | 40 | | | 160 | 150 | | 50 | 50 | 60 | 160 | 60 | 35 |
| 9 | 65 | | 80 | 30 | 250 | | 90 | 95 | | 105 | 45 | 60 | | 250 | | 60 | 30 | | | 160 | 175 | | 55 | 50 | 60 | 180 | 65 | |
| 10 | 60 | | 80 | 43 | 275 | 100 | 100 | 105 | | 105 | 45 | 60 | | | | | 30 | | | | 200 | 35 | 55 | 55 | | 180 | 90 | 35 |
| 11 | 80 | | 85 | 43 | 275 | 120 | | 120 | | 100 | 45 | 60 | | | 35 | | | 50 | 80 | | 200 | 50 | | | | 200 | 30 | 35 |
| 12 | 85 | | 90 | 43 | 300 | 120 | 110 | 135 | | 100 | 45 | 75 | | | 40 | | | 75 | | | | | 60 | | 65 | 225 | 85 | 35 |
| 13 | 95 | | 100 | 45 | 310 | | | | | 100 | 45 | 75 | | | 45 | | | 100 | 90 | | | | | 60 | | | 90 | 35 |
| 14 | 105 | | | 45 | 310 | | | 150 | | | 60 | 80 | | | | 50 | | 115 | | | | | 70 | 60 | | | 100 | 35 |
| 15 | 115 | | | 45 | 310 | | 120 | | 150 | | 60 | 85 | | | 45 | 65 | | | | | | | | 60 | 65 | 250 | 115 | 35 |
| 16 | 115 | | | 46 | 310 | 120 | | 175 | 175 | | 70 | 95 | | | 50 | 55 | | 130 | | | | | 70 | 60 | | | 120 | 35 |
| 17 | 130 | | | 60 | 330 | | | 190 | | | 75 | 105 | | | 55 | 60 | | 145 | | | | 55 | | 60 | | | 130 | 40 |
| 18 | 130 | | | 70 | 290 | | 135 | | 185 | 110 | 85 | 110 | | | 55 | 70 | | 160 | | | | | | 55 | | 250 | 70 | 40 |
| 19 | 140 | | | 80 | 240 | | 150 | | 185 | 120 | 95 | 115 | | | 55 | | | | | | | | | 55 | | | 70 | 50 |
| 20 | 140 | | | 70 | 240 | 120 | 165 | | 200 | 135 | 105 | 120 | | 250 | | | | 200 | | | | 50 | | 60 | | 250 | | 55 |
| 21 | 140 | | | 70 | 240 | | 180 | | 220 | 110 | 110 | 120 | | 275 | | | | 200 | 90 | | | 55 | | | | 275 | 85 | 55 |
| 22 | 150 | | | 70 | 240 | 120 | | | 240 | 110 | 125 | 125 | | 300 | | | | 225 | 105 | | | | | | 65 | | 95 | 65 |
| 23 | 150 | | | | 240 | 140 | | | 200 | | 130 | 125 | | 300 | | | | 250 | | | | | | | 60 | | 110 | 75 |
| 24 | 150 | | | 90 | 240 | 140 | 135 | | 210 | | 140 | 125 | | | 55 | | | | | | | 65 | | | 80 | 300 | | 80 |
| 25 | 160 | | | | | | 150 | 175 | 185 | | 150 | 140 | | | | | | | | | | 60 | | 40 | 70 | | 110 | 90 |
| 26 | 160 | | | | 240 | 140 | 165 | 190 | 195 | | 150 | 150 | | | 60 | | | | | | | | | 40 | 80 | 300 | | 70 |
| 27 | | | | | | | 180 | | 195 | | 160 | 150 | | | | | | 200 | | | | | | 50 | | | | 100 |
| 28 | | | | 105 | | 150 | | | 200 | | 170 | 150 | | 250 | | | | 200 | 105 | | | 60 | | | 60 | | 110 | 115 |
| 29 | | | | 120 | | 150 | | | 220 | | 190 | 175 | | 275 | 50 | | | 225 | 115 | | | | | 60 | | | | 125 |
| 30 | | | | 135 | | | | | 240 | | | 175 | | 300 | 55 | | | 250 | | | | | | | | 325 | | 135 |
| 31 | | | | 150 | | | | | 200 | | 210 | 170 | | 300 | | | | | | | | 60 | | 60 | | | | 150 |
| 32 | 100 | | | | | | | | 210 | | 230 | | | | 60 | | | | | | | | | | | | | 130 |
| 33 | | | | | | | | | 185 | | | 170 | | | 55 | 30 | | | | | | | | | | | | 140 |
| 34 | 120 | | | | | 150 | | | 195 | | | 180 | | | 55 | 40 | | | 115 | | | | | 55 | | | | 140 |
| 35 | | | | | | | | | 195 | | 230 | 170 | | | | 50 | | | | | | | | 50 | | | | 150 |
| 36 | | | | | | | | | 200 | | | | | | | | | | | | | | | 70 | | | | 150 |
| 37 | | | | 150 | | | | | 200 | | 250 | 180 | | | | | | | 130 | | | | | | | | 80 | 165 |
| 38 | | | | 165 | | | | | 215 | | | | | | | | | | 130 | | | | | | | | | 180 |
| 39 | | | | 160 | | | | | 200 | | 250 | | | | | | | | 130 | | | | | 70 | | | 80 | 180 |
| 40 | | | | | | | | | 200 | | | | | | | | | | | | | | | | | | 95 | 195 |

TABLE 2-continued

| Week | B23 | B26 | B3 | B6 | C11 | D20 | D8 | H2 | K10 | M12 | M19 | M25 | M33 | N13 | N14 | N30 | N7 | O34 | Q9 | R17 | R32 | S1 | S36 | T15 | T29 | W24 | Z27 | Z34 |
|---|---|---|---|---|---|---|---|---|---|---|---|---|---|---|---|---|---|---|---|---|---|---|---|---|---|---|---|---|
| ID | Y | Y | Y | Y | N | N | Y | Y | Y | Y | Y | Y | N | N | Y | N | N | Y | Y | N | N | Y | Y | Y | Y | N | Y | Y |
| | | | | | | | | | | | | | | PT days | PT weeks | | | | | | | | | | | | | |
| | | | | | | | | | | | | | | | Dose (mg, Ketamine) | | | | | | | | | | | | | |
| 41 | | | | 175 | | | | | 200 | | 250 | | | | | | | | | | | | | | | | | 150 |
| 42 | | | | | | | | | 210 | | | | | | | | | | | | | | | | | | | 165 |
| 43 | | | | | | | | | 215 | | | | | | | | | | | | | | | | | | | |
| 44 | | | | | | | | | 215 | | | | | | | | | | | | | | | | | | | |
| 45 | | | | 185 | | | | | 215 | | | | | | | | | | | | | | | | | | | |
| 46 | | 75 | | | | | | | | | | | | | | | | | | | | 60 | | | | | 95 | |
| 47 | | 90 | | | | | | | | | | | | | 40 | | | | | | | | | 70 | | | 90 | |
| 48 | | | | | | | | | | | | | | | | | | | | | | | | | | | 90 | |
| 49 | | | | | | | | | 215 | | | | | | 50 | | | | | | | 60 | | | | | 105 | |
| 50 | | | | | | | | | 215 | | | 180 | | | 55 | | | | | | | 60 | | | | | 95 | |
| 51 | | | | | | | | | 215 | | | 190 | | | 60 | | | | | | | | | | | | | |
| 52 | | | | | | | | | 215 | | | 200 | | | 70 | | | | 130 | | | 60 | | | | | 95 | 165 |
| 53 | | | | | | | | | 200 | | | 215 | | | 65 | | | | | | | | | | | | 95 | |
| 54 | | | | | | | | | 200 | | | 220 | | | 65 | | | | | | | 60 | | | | | 110 | |
| 55 | | | | | | | | | | | | 220 | | | | | | | | | | | | | | | | |
| 56 | | | | | | | | | | | | 235 | | | 65 | | | | | | | | | | | | | 175 |
| 57 | | | | | | | | | | | | 235 | | | 75 | | | | 130 | | | | | | | | | 190 |
| 58 | | 90 | | | | | | | | | | 240 | | | 85 | | | | 130 | | | | | | | | 120 | 200 |
| 59 | | 120 | | | | | | | | | | | | | 80 | | | | 130 | | | | | | | | | 200 |
| 60 | | | | | | | | | | | | | | | 75 | | | | | | | | | | | | | |
| 61 | | | | | | | | | | | | 240 | | | | | | | | | | | | | | | 120 | |
| 62 | | | | | | | | | | | | | | | | | | | | | | | | | | | 120 | |
| 63 | | | | | | | | | | | | | | | | | | | | | | | | | | | | |
| 64 | | | | | | | | | | | | | | | | | | | | | | | | | 60 | | | 200 |
| 65 | | | | | | | | | | | | | | | 80 | | | | | | | | | | 60 | | | |
| 66 | | | | | | | | | | | | | | | | | | | | | | | | | | | 130 | 220 |
| 68 | | | | | | | | | | | | | | | 80 | | | | | | | | | | | | 140 | 220 |
| 69 | | | | | | | | | | | | 250 | | | 80 | | | | | | | | | | | | 140 | 220 |
| 72 | | | | | | | | | | | | | | | | | | | | | | | | | | | 145 | 220 |
| 73 | | | | | | | | | | | | | | | | | | | | | | | | | | | 150 | 220 |
| 75 | | | | | | | | | | | | | | | | | | | | | | | | | | | 150 | 225 |
| 76 | | | | | | | | | | | | | | | | | | | | | | | | | | | | 250 |
| 77 | | | | | | | | | | | | | | | | | | | | | | | | | | | | 275 |
| 78 | | | | | | | | | | | | | | | | | | | | | | | | | | | | 300 |
| 79 | | | | | | | | | | | | | | | | | | | | | | | | | | | | 300 |
| 81 | | | | | | | | | | | | 250 | | | | | | | | | | | | | | | | 325 |
| 82 | | | | | | | | | | | | | | | | | | | | | | | | | | | | 325 |

The invention claimed is:

1. A method for treating pain, the method comprising, a combination therapy comprising:
administering intravenously, intramuscularly, orally, intranasally or by inhalation an N-methyl d-aspartate receptor (NMDAR) antagonist to an individual having pain, and
applying, external to the skull of the individual, transcranial magnetic stimulation (TMS) therapy directed towards the anterior cingulate region.

2. The method of claim 1, wherein the TMS is applied at least one of prior to, during and after the administration of the NMDAR antagonist as part of the combination therapy.

3. The method of claim 1, wherein the NMDAR antagonist is ketamine.

4. The method of claim 3, wherein the ketamine is administered at a dose of about 50 mg to about 500 mg.

5. The method of claim 3, wherein the ketamine is administered at a dose of about 0.5 mg/kg to about 5.0 mg/kg.

6. The method of claim 1, wherein the TMS is applied at intervals of 3-7 days during the administration of the NMDAR antagonist.

7. The method of claim 1, wherein the pain is associated with Complex Regional Pain Syndrome or Reflex Sympathetic Dystrophy.

8. The method of claim 1, wherein the individual having pain has previously failed at least one of the following treatments: rTMS alone, vagus nerve stimulation (VNS), TLVES alone, electroconvulsive therapy (ECT), hyperbaric oxygen, ketamine alone, and homeopathy.

9. The method of claim 1, wherein the TLVES or TMS is applied up to four days after administration of the NMDAR antagonist.

10. The method of claim 1, wherein the TLVES or TMS is applied within two hours after administration of the NMDAR antagonist.

11. A method for treating depression, comprising a combination therapy comprising:
administering intravenously, intramuscularly, orally, intranasally or by inhalation an N-methyl d-aspartate receptor (NMDAR) antagonist to a patient suffering from depression, and
applying, external to the skull of the patient, transcranial low voltage electric stimulation (TLVES) therapy comprising 1-4 mAmps applied across brain tissue or transcranial magnetic stimulation (TMS) therapy directed towards the anterior cingulate region.

12. The method of claim 11, wherein the TLVES or TMS is applied at least one of prior to, during and after the administration of the NMDAR antagonist as part of the combination therapy.

13. The method of claim 11, wherein the NMDAR antagonist is ketamine, d-cycloserine, or dextromethorphan.

14. The method of claim 13, wherein the ketamine is administered at a dose of about 50 mg to about 500 mg.

15. The method of claim 13, wherein ketamine is administered at a dose of about 0.5 mg/kg to about 5.0 mg/kg.

16. The method of claim 11 wherein the TLVES or TMS is applied at intervals of 3-7 days during the administration of the NMDAR antagonist.

17. The method of claim 11, wherein the depression is bipolar depression.

18. The method of claim 11, wherein the depression is major depressive disorder.

19. The method of claim 11, wherein the patient has previously failed at least one of the following treatments: rTMS alone, VNS, TLVES alone, ECT, hyperbaric oxygen, ketamine alone, and homeopathy.

20. The method of claim 11, wherein the TLVES or TMS is applied up to four days after administration of the NMDAR antagonist.

21. The method of claim 11, wherein the TLVES or TMS is applied within two hours after administration of the NMDAR antagonist.

22. A method for treating pain, the method comprising a combination therapy comprising:
administering a NMDAR antagonist intravenously, intramuscularly, orally, intranasally or by inhalation to an individual having pain, and
applying, external to the skull of the individual, transcranial low voltage electric stimulation (TLVES) therapy comprising 1-4 mAmps applied across brain tissue.

23. The method of claim 22, wherein the TLVES is applied at least one of prior to, during and after the administration of the NMDAR antagonist as part of the combination therapy.

24. The method of claim 22, wherein the pain is associated with Complex Regional Pain Syndrome or Reflex Sympathetic Dystrophy.

25. The method of claim 22, wherein the TLVES is applied at intervals of 3-7 days during the administration of the NMDAR antagonist.

26. The method of claim 22, wherein the patient has previously failed at least one of the following treatments: rTMS alone, VNS, TLVES alone, ECT, hyperbaric oxygen, ketamine alone, and homeopathy.

27. The method of claim 22, wherein the TLVES or TMS is applied up to four days after administration of the NMDAR antagonist.

28. The method of claim 22, wherein the TLVES or TMS is applied within two hours after administration of the NMDAR antagonist.

29. The method of claim 22, wherein the NMDAR antagonist is ketamine, d-cycloserine, or dextromethorphan.

30. The method of claim 29, wherein the ketamine is administered at a dose of about 50 mg to about 500 mg.

31. The method of claim 29 wherein the ketamine is administered at a dose of about 0.5 mg/kg to about 5.0 mg/kg.

32. A method for treating substance abuse, comprising:
a combination therapy comprising:
administering intravenously, intramuscularly, orally, intranasally or by inhalation an N-methyl d-aspartate receptor (NMDAR) antagonist to a patient suffering from substance abuse, and
applying, external to the skull of the patient, transcranial stimulation therapy selected from transcranial low voltage electric stimulation (TLVES) therapy comprising 1-4 mAmps applied across brain tissue or transcranial magnetic stimulation (TMS) therapy directed towards the anterior cingulate region.

33. The method of claim 32, wherein the TLVES or TMS is applied up to four days after administration of the NMDAR antagonist.

34. The method of claim 32, wherein the TLVES or TMS is applied within two hours after administration of the NMDAR antagonist.

35. A method for treating obsessive compulsive disorder (OCD), comprising:
- a combination therapy comprising:
- administering intravenously, intramuscularly, orally, intranasally or by inhalation an N-methyl d-aspartate receptor (NMDAR) antagonist to an individual exhibiting OCD, and
- applying external to the skull of the individual, transcranial stimulation therapy selected from transcranial low voltage electric stimulation (TLVES) therapy comprising 1-4 mAmps applied across brain tissue or transcranial magnetic stimulation (TMS) therapy directed towards the anterior cingulate region.

36. The method of claim 35, wherein the TLVES or TMS is applied up to four days after administration of the NMDAR antagonist.

37. The method of claim 35 wherein the TLVES or TMS is applied within two hours after administration of the NMDAR antagonist.

38. A method for treating tinnitus, comprising a combination therapy comprising:
- administering intravenously, intramuscularly, orally, intranasally or by inhalation an N-methyl d-aspartate receptor (NMDAR) antagonist to an individual suffering from tinnitus, and
- applying external to the skull of the individual, transcranial stimulation therapy selected from transcranial low voltage electric stimulation (TLVES) comprising 1-4 mAmps applied across brain tissue or transcranial magnetic stimulation (TMS) therapy directed towards the anterior cingulate region.

39. The method of claim 38, wherein the TLVES or TMS is applied up to four days after administration of the NMDAR antagonist.

40. The method claim 38 wherein the TLVES or TMS is applied within two hours after administration of the NMDAR antagonist.

* * * * *